United States Patent [19]

Boksay et al.

[11] 4,312,861
[45] Jan. 26, 1982

[54] PHARMACEUTICAL COMPOSITIONS CONTAINING N-ALKYL-N-(NUCLEARLY-SUBSTITUTED) BENZYLAMINES HAVING VASOTONIA-REGULATING ACTIVITY

[75] Inventors: Istvan Boksay, Kiedrich; Alfons Söder, Frankfurt-Schwanheim; Volkher Bollmann, Erbach; Rolf-Ortwin Weber, Naurod, all of Fed. Rep. of Germany

[73] Assignee: Hoechst Aktiengesellschaft, Frankfurt am Main, Fed. Rep. of Germany

[21] Appl. No.: 806,272

[22] Filed: Jun. 13, 1977

Related U.S. Application Data

[63] Continuation of Ser. No. 555,104, Mar. 4, 1975, abandoned.

[30] Foreign Application Priority Data

Mar. 9, 1974 [DE] Fed. Rep. of Germany ....... 2411406
Jun. 14, 1974 [DE] Fed. Rep. of Germany ....... 2428625

[51] Int. Cl.$^3$ .................... A01N 33/02; A01N 57/00; A61K 31/66; A61K 31/135
[52] U.S. Cl. ............................. 424/220; 260/501.12; 424/330; 564/15; 564/336; 564/346; 564/373
[58] Field of Search .......................... 260/570.9, 570.6; 424/330, 220; 564/15, 17, 336, 346, 373

[56] References Cited

U.S. PATENT DOCUMENTS

| | | | |
|---|---|---|---|
| 2,229,187 | 1/1941 | Peyer | 260/572 |
| 2,374,807 | 5/1945 | Dickey | 260/560 |
| 2,608,584 | 8/1952 | Sprules et al. | 260/570.9 |
| 2,613,226 | 10/1952 | Craig et al. | 260/570.9 |
| 2,732,402 | 1/1956 | Surrey | 260/562 |
| 2,732,403 | 1/1956 | Surrey | 260/562 |
| 2,847,442 | 8/1958 | Sallman | 260/459 |
| 2,852,562 | 9/1958 | Surrey | 260/570.9 |
| 2,862,967 | 12/1958 | Surrey | 260/562 |
| 2,999,872 | 9/1961 | Craig et al. | 260/429 |
| 3,336,308 | 8/1967 | Keck | 260/247.5 |
| 3,345,309 | 10/1967 | Merten et al. | 260/570.9 X |
| 3,406,024 | 10/1968 | Richter et al. | 260/570.9 X |

OTHER PUBLICATIONS

Matter, Chemical Abstracts, vol. 45, cols. 4399 and 4400 (1951).
Shapiro et al., J. Amer. Chem. Soc., vol. 81, pp. 3728 to 3736 (1959).
Surrey et al., J. Amer. Chem. Soc., vol. 77, pp. 3798 to 3801 (1955).
Takeuchi et al., Index Chemicus, vol. 33, 111476 (1969).
Lewis et al., Chemical Abstracts, vol. 40, cols. 4144 to 4145 (1946).
Buck et al., J. Am. Chem. Soc., vol. 63, pp. 1964 to 1966 (1941).
Chemische, Chemical Abstracts, vol. 34, col. 7296 (1940).
Gupta et al., Index Chemicus, vol. 26, 84289 (1967).

*Primary Examiner*—Floyd D. Higel
*Attorney, Agent, or Firm*—Berman, Aisenberg & Platt

[57] ABSTRACT

Aralkylamines of the formula:

$$R^1-CH_2-N(R^3)-R^2$$

wherein
R$^1$ is a phenyl substituted by one of:
 (I) alkyls,
 (II) halo and
 (III) nitro;
R$^2$ is
 (IV) alkyl having from 4 to 10 carbon atoms, four of which are in one chain,
 (V) alkyl interrupted by an oxygen atom, i.e. an alkoxyalkyl or ether radical, or
 (VI) hydroxyalkyl wherein the alkyl is either (IV) or (V) and the hydroxy is the sole substituent;
R$^3$ is a hydrogen atom, alkyl having from 1 to 4 carbon atoms or such alkyl substituted by a dialkylphosphinyl group;

a physiologically-compatible acid-addition salt thereof and a pharmaceutical composition containing such compound(s) as active ingredient(s) are valuable in view of the physiological activity, e.g. vasotonic, capillary sealing and antiarrhythmic, of the aralkylamines and their physiologically-compatible acid-addition salts.

2 Claims, No Drawings

PHARMACEUTICAL COMPOSITIONS CONTAINING N-ALKYL-N-(NUCLEARLY-SUBSTITUTED) BENZYLAMINES HAVING VASOTONIA-REGULATING ACTIVITY

The present application is a continuation of application Ser. No. 555,104, filed Mar. 4th, 1975, and now abandoned.

This invention relates to certain new aralkylamines having interesting physiological properties and to processes for their preparation.

Substituted hexylamines, e.g. 2-isopropyl-amino-6-methylheptane and N-2-cyclohexylethyl-hexylamine have already been used in the form of their hydrochlorides as pharmaceuticals with an antihistaminic or vasodilatoric effectivity.

The reductive alkylation of amines, such as with excessive sodium cyano-boronhydride and formaldehyde is acetonitrile, with formaldehyde and formic acid or with formaldehyde, hydrogen and palladium-coal in the presence of water is known as well as the reaction of amines with sodium in pyridine and the ethylation of the amino group with ethylene.

According to one feature of the present invention there are provided compounds of general formula

wherein
$R^1$ represents a phenyl group substituted by 2,3 or 4 identical or different alkyl groups having 1 to 4 carbon atoms, said alkyl substituents having in total not more than 6 carbon atoms and any alkyl substituent in the p-position being separated from any other alkyl substituent by a vacant m-position, or a phenyl group substituted by one or two halogen atoms or nitro groups with the proviso that any fluoro substituent is situated in the p-position and if the phenyl group has two halogen substituents these are both situated in the o-positions, said o-, m- and p-positions being referred to the point of attachment to the aminomethylene group,
$R^2$ represents a straight-chain or branched alkyl group having 4 to 10 carbon atoms and at least 4 carbon atoms in one chain, said alkyl group being optionally interrupted by an oxygen atom and/or being optionally substituted by a hydroxy group, said alkyl group
  (a) being branched in the β-position to the nitrogen atom only if there is further branching of the chain,
  (b) having no more than 3 chain branchings, and
  (c) having a single methyl substituent or no substituent in the α-position to the nitrogen atom, and
$R^3$ represents a hydrogen atom or an alkyl group having 1 to 4 carbon atoms being unsubstituted or substituted by a dialkylphosphinyl group of formula

(wherein $R^4$ and $R^5$ represent alkyl groups having in total 2 to 6 carbon atoms) and physiologically compatible acid addition salts thereof.

In general the compounds according to the present invention have valuable physiological properties, in particular one or more activities selected from a vasotonic, capillary sealing and antiarrhythmic activity.

Preferred compounds of general formula I by virtue of their particularly effective physiological properties are those wherein $R^1$ represents a phenyl group having 3 alkyl substituents in the o- and p-positions and those wherein $R^2$ represents an alkyl group having from 5 to 8 carbon atoms, preferably up to 7 carbon atoms, being free of hydroxyl substituents and uninterrupted by oxygen atoms, and preferably having an α-methyl substituent.

Compounds of general formula I according to the invention wherein $R^2$ represents a branched alkyl group wherein the alkyl substituents on the main chain are vicinal or separated by 1,3,4 or 5 carbon atoms and those wherein $R^2$ represents an unbranched alkyl group having 4 to 6 or 8 to 10 carbon atoms being interrupted by an oxygen are also particularly effective. Those compounds of general formula I wherein $R^2$ represents a branched alkyl group being interrupted by an oxygen atom also have good physiological properties.

According to the further features of the present invention there are provided the following processes for the preparation of the new compounds of general formula I according to the invention:

(a) Reaction of a compound of formula

with a compound of formula

or (b) Reaction of a compound of formula

with a compound of formula

or (c) Reaction of a compound of formula

with a compound of formula

or (d) Reduction of a compound of formula

or of formula

or of formula

or of formula

whereby a compound of formula I as hereinbefore defined is obtained, or (e) by an alkylation of an amine of formula VII in a per se known manner, e.g. with an alkyl ester of sulfuric acid, [wherein $R^1$, $R^2$ and $R^3$ are as hereinbefore defined with the proviso that in process (c) $R^3$ does not represent a hydrogen atom, X represents a halogen atom or an alkylsulfonyloxy or arylsulfonyloxy group, $R^6$ is as hereinbefore defined for $R^2$ but has one carbon atom less than $R^2$, $R^7$ represents an alkyl group having 1 to 3 carbon atoms optionally substituted by a dialkylphosphinyl group of formula

(wherein $R^4$ and $R^5$ are as hereinbefore defined)]: and if desired subsequently converting a compound of formula I obtained thereby into a physiologically compatible acid addition salt.

Examples of compounds of general formula II which may be used in process (a) are the following: 3,4,5-trimethylbenzyl chloride, 2,4,6-trimethylbenzyl chloride, 2,3,5,6-tetramethylbenzyl bromide, 4-tert.-butyl-2,6-dimethylbenzyl iodide, 3-tert.-butyl-6-methylbenzyl chloride, 4-chlorobenzyl chloride, 3-chlorobenzyl chloride, 2-chlorobenzyl chloride, 2,6-dichlorobenzyl chloride, 3-bromobenzyl chloride, 2-bromobenzyl chloride, 4-nitrobenzyl chloride, esters of 2,4,6-trimethylbenzyl-toluene sulphonic acid, and 4-fluorobenzyl chloride.

Examples of compounds of general formula IV are the following: 1-, 2- and 3-chloro-, -bromo- and -iodo-, -pentane, -hexane, -heptane, -octane, -nonane and -decane, 1-chloro-4-methylpentane, 1-chloro-2-ethylhexane, 2-chloro-3-methylpentane, 2-iodo-6-methylheptane, 2-chloro-5-hydroxy-5-methylheptane, 2-bromo-2,4,4-trimethylpentane, 3-chloropropyl ethyl ether, 3-chloropropyl butyl ether, 3-chloropropyl hexyl ether, 3-chloropropyl isopropyl ether and hept-2-yltoluene sulphonic acid esters.

Compounds of general formula VI include for example methyl iodide, propyl bromide, n- and isobutyl chloride and dimethylphosphinylmethyl chloride.

Amines of general formula III include e.g. the following straight-chain compounds: 1-, 2- and 3-aminopentane, hexane, -heptane, -octane, -nonane and -decane, and also the following branched compounds: 1-, 2- and 5-amino-4-methylpentane, 1-amino-2-ethylhexane, 2-amino-3-methylpentane, 2-amino-5-methylhexane, 2-amino-4-methylhexane, 2-amino-6-methylheptane, 2-amino-5-hydroxy-5-methylheptane, 2-amino-2,4,4-trimethylpentane, 3-aminopropyl ethyl ether, 3-aminopropyl hexyl ether, 3-aminopropyl isopropyl ether, 2-methyl-aminoheptane, 2-propylaminoheptane, 2-dimethylphosphinylmethylaminoheptane, 2-amino-n-nonane, 2-amino-n-decane, 3-amino-n-octane, 2-amino-7-methyl-octane, 2-amino-3,6-dimethylheptane.

The following are examples of amines of general formula V: 3,4,5-trimethylbenzylamine, 2,4,6-trimethylbenzylamine, 2,3,5,6-tetramethylbenzylamine, 4-tert.-butyl-2,6-dimethylbenzylamine, 3-tert.-butyl-6-methylbenzylamine, 4-fluorobenzylamine, 4-chlorobenzylamine, 3-chlorobenzylamine, 2-chlorobenzylamine, 2,6-dichlorobenzylamine, 3-bromobenzylamine, 2-bromobenzylamine, 4-nitrobenzylamine, and also the corresponding secondary amines which are substituted at the nitrogen atoms, for example with a methyl, ethyl, propyl, dimethylphosphinylmethyl or dimethylphosphinylpropyl group.

An amine of formula VII is for example 2-(2,4,6-trimethylbenzyl)-aminoheptane.

Certain of the compounds of general formula I contain at least one asymmetric carbon atoms, and it is to be understood that the pure optically active isomers as well as their racemates lie within the scope of the present invention.

Processes (a) to (e) according to the invention may conveniently be effected in the pesence of a solvent being inert to the reaction components, preferably an alcohol with 1 to 4 carbon atoms, an aromatic hydrocarbon, such as benzene, toluene, xylene or mesitylene, or dimethylformamide. Reaction in the presence of a solvent is particularly preferred when reacting alkyl esters of mineral acids and organic sulphonic acids. The reaction is advantageously effected in the presence of an acid acceptor, preferably an at least equimolar quantity of at least one alkali metal carbonate or a tertiary amine, or in the presence of an at least equimolar excess of the amine of formula III, V or VII used. In general, the process especially the variants (a) to (c) and (e), is performed at temperatures from 50° to 160° C., preferably 75° to 135° C. If dimethylformamide is used as the solvent, no acid acceptor is required, but usually a temperature of 70° to 160° C. is necessary.

Examples of alkali metal carbonates which may be used as acid acceptors are sodium hydrogen carbonate, sodium carbonate and potassium carbonate. Of the large number of tertiary amines which may be used, diisopropylamine, tributylamine, triethylamine, picoline and pyridine have proved especially effective. When an aralkyl chloride is reacted, the reaction may be accelerated by adding a small amount of sodium iodide.

The preparation of alkylamines of general formula I wherein $R^3$ represents an alkyl group, in particular a methyl or ethyl group, according to process (c) may be effected under the usual reaction conditions.

The reduction of the amides of general formula X, XI and XII, is effected in per se known manner, for example in tetrahydrofuran or in a dialkyl ether, such as diethyl, diisopropyl or dibutyl ether, preferably at the boiling point of the solvent used, by means of a metal hydride, such as lithium aluminium hydride, or a boron hydride such as diborane. Decomposition of the amide/hydride adduct which is not isolated may be conveniently effected with ethyl acetate, water or saturated sodium sulphate solution.

Reduction of the thioamides of general formula XIII, is again effected in per se known manner, for example by treating with Raney nickel or by electrolytic reduction in the presence of a solvent, such as dioxane, acetone or an alcohol having 1 to 4 carbon atoms or an aqueous mixture thereof.

It is also possible according to the process (c) or (e) to react a compound of formula VII which has been prepared by reducing a compound of formula $$R^1-CH=N-R^2 \quad (VIII)$$

or formula $$R^1-CH_2-N=R^8 \quad (IX)$$

wherein $R^1$ and $R^2$ are as defined in claim 1 and $R^8$ represents an alkylidene group having one hydrogen atom less than the uninterrupted and unsubstituted alkyl radical $R^2$ but otherwise identical therewith.

Compounds of general formula I as hereinbefore defined wherein $R^3$ represents a hydrogen atom may be prepared by process (c) and (e) according to the invention. The reduction is conveniently effected with sodium or sodium amalgam in alcohol or zinc in acetic acid or electrolytically at lead or copper cathode. The process may also be effected as part of a reductive alkylation process (see "Organic Reactions", Vol IV, pp 174 ff) wherein the catalytic hydrogen addition is effected in the presence of a catalyst such as platinum, palladium, nickel or cobalt.

The compounds of general formula I according to the invention may if desired be converted into their physiologically compatible acid addition salts by reaction with a appropriate acid, for example hydrochloric acid, nitric acid, phosphoric acid, sulfuric acid, cyclohexylsulfamic acid, gluconic acid, citric acid, maleic acid and adipic acid.

In general the new compounds according to the invention show a valuable vasotonia-regulating activity. They increase vasotonia without inducing spasms, dilate the blood vessels, reduce the increased permeability of the blood vessels and may induce an anti-oedematous and analgesic activity. They also in general have a good compatibility.

The compounds shown in Table I enclosed have for example been tested with regard to their physiological activities.

Pharmacological tests (1) Isolated vein and aorta sections

The tests were carried out on isolated vein and aorta sections from rabbits in accordance with the modified method of Furchgott et al (J. Pharmacol, exp. Ther. 108 (1953), page 129). The results are given in Tables 2 and 3. The contraction of the vein section in adrenalin and of the aorta section in noradrenalin, after administration of $10^{-6}$ g/ml of the test compound was defined to have the base value of 100.

(2) Isolated rat's portal vein

The tests on the rat's portal vein, an organ with its own rhythm, were performed according to the method of Berti et al (Arch. int. Pharmacodyn. 184 (1970), page 328). In Table 4, the increase in tonus at various adrenalin concentrations is given in milligrams. As a comparison, the values for the known substance heptaminol (=6-amino-2-methylheptane-2-ol) are also given.

(3) Blood-flow change in an isolated rabbit ear

The tests were carried out according to Krakow-Pissemski (Pflügers Archiv 151 (1913), page 583 and 156 (1914), page 426). In Table 5a the estimated values of the vaso-constrictor activity in Ringer solutions of varying concentrations are given and in Table 5b values for vasodilatory activity in Ringer-Norfenefrin solutions of varying concentrations are given. As a comparison, the values obtained with the known preparation aescin sodium are given.

(4) Relative coronary blood-flow change in an isolated guinea-pig heart.

The tests were carried out according to the method of Langendorff (Pflügers Archiv. 61 (1895), page 219).

In Table 5, the change in coronary blood flow after administration of various quantities of the test substance is compared with that after administration of the known compounds heptaminol and Aescin sodium salt.

(5) Histamine rash test

The test according to Halpern (Presse médicale 65 (1949), page 949) was used in modified form. The suppressive effect of the compounds according to the invention on the permeability of the capillaries was tested. The blue coloration induced by intravenous administration of trypan blue at two intracutaneous histamine injection points per animal, (trypan blue administered 2 minutes before the histamine), was estimated according to the following scale of values:

| | |
|---|---|
| no blue coloration | =0 |
| indications of blue coloration | =2 |
| clear blue coloration | =4 |
| stong blue coloration | =6 |

The preceding evaluation was made from the combined effect at the two injection points.

The test substances were administered i.p. 30 minutes before the histamine injection. The results with the compounds according to the invention and also with aescin sodium as a control are shown in Table 7. The control substance aescin sodium was administered 16 hours before the injection for optimum effectiveness in order to obtain comparable results.

(6) Toxicity in the mouse

Toxicity was determined according to Litchfield and Wilcoxon (J. Pharmacol. exp. Ther. 97 (1949), page 399) in the mouse. In comparison, the values with the known substance aescin sodium salt were determined. The results are given in Table 7. Comparative tests with 0.1% solution, of venous and optical compatibility on the rabbit yielded similar results.

(7) Suppression of carrageenin oedema in the rat paw

The inflammation-reducing and anti-oedematous effects on carrageenin and serotonin oedemas in the rat paw were studied according to Siegmund et al (Proc. Soc. exp. Biol. Med. 95 (1957), page 729). The values are given as percentages, based on the values obtained in control tests using a dummy procedure. In this way, the antiphlogistic activity of the substances according to the invention was tested. The results are given in Table 8.

(8) Writhing Test

The analgesic activity of the compounds according to the invention were studied by the method of Winter et al (Proc. Soc. exp. Biol. Med, 111 (1962), page 544), in which the suppression of writhing movements in the mouse was observed. The results are assembled in Table 9.

(9) Hot-plate Test

This test was performed on the mouse, according to Chen and Beckman (see Science 113 (1951), page 631). 50 mg/kg of the compound No. 2 (cf. formula sheet) which has been administered per os increase the reaction time of the animals by 70%. In comparison thereto for the effective dose of 50% (ED 50) the necessary quantity of the comparison substance aminophenazone was found to be 84 mg/kg.

TABLE 2

Isolated vein section

| Serial No. | 2 | 3 | 4 | 6 | 12 | 13 | 14 | 22 | 26 | 27 | 28 | 30 | Aescin sodium salt (comparison) |
|---|---|---|---|---|---|---|---|---|---|---|---|---|---|
| g/ml | | | | | | | | | | | | | |
| $10^{-5}$ | | | | | | | | 4 | | 14 | | | 13 |
| $3 \times 10^{-5}$ | 15 | | | | | | | 8 | | 28 | | | |
| $10^{-4}$ | 16 | 18 | 6 | $16^{(+)}$ | 20 | 14 | $18^{(+)}$ | | $60^{(+)}$ | 19 | 20 | 19 | 13 |
| $1.6 \times 10^{-4}$ | 32 | | 16 | | | | | | | 30 | | | |

$^{(+)}$Test substance dissolved in propanediol

TABLE 3

Isolated aorta section

| Serial No. | 2 | 3 | 4 | 10 | 22 | 24 | 27 | 28 | Aescin sodium salt (comparison) |
|---|---|---|---|---|---|---|---|---|---|
| g/ml | | | | | | | | | |

TABLE 3-continued

Isolated aorta section

| Serial No. | 2 | 3 | 4 | 10 | 22 | 24 | 27 | 28 | Aescin sodium salt (comparison) |
|---|---|---|---|---|---|---|---|---|---|
| $10^{-4}$ | 10 | 19 | 22 | 9 | 15 | 15 | 18 | 14 | 0 |

TABLE 4

Isolated rat's cortal vein

| g/ml | Serial no. 2 | 22 | 27 | 28 | Heptaminol (comparison) |
|---|---|---|---|---|---|
| $10^{-6}$ | | +65 | −9 | +21 | +9 |
| $10^{-5}$ | +106 | +225 | +19 | +57 | +9 |
| $10^{-4}$ | +185 | +271 | +250 | +84 | +47 |

TABLE 5

Relative change in blood flow in a perfused rabbit ear (vaso-constrictor activity)

| g/ml | 2 | 3 | 4 | 7 | 8 | 12 | 14 | 20 | 22 | Aescin sodium salt (comp.) |
|---|---|---|---|---|---|---|---|---|---|---|
| (a) Vaso-constrictor activity (Ringer solution) | | | | | | | | | | |
| $10^{-6}$ | | | | | | | | | | −6 |
| $3 \times 10^{-6}$ | | | | | | | | | | −33 |
| $10^{-5}$ | | | | | | | | | −2 | −92 |
| $3 \times 10^{-5}$ | 0 | 0 | +8 | | | | −5 | 0 | | |
| $10^{-4}$ | 0 | | 0 | | | | | | −42 | |
| (b) Vaso-dilator activity (Ringer-Norfenefrin solution) | | | | | | | | | | |
| $10^{-7}$ | +3 | +3 | +4 | | | | | | | |
| $10^{-6}$ | +31 | +43 | +40 | | +3 | | | +12 | | |
| $3 \times 10^{-6}$ | | | | | | | | | | |
| $10^{-5}$ | +73 | +105 | +104 | | | | | +4 | | |
| $3 \times 10^{-5}$ | | +38 | +31 | +34 | +66 | +12 | | +30 | 0 | 0 |
| $10^{-4}$ | +112 | | | | | | | +131 | | (++) |

| g/ml | Serial no. 23 | 25 | 26 | 27 | 28 | 29 | 30 | 31 | Aescin sodium salt (comp.) |
|---|---|---|---|---|---|---|---|---|---|
| (a) Vaso-constrictor activity (Ringer solution) | | | | | | | | | |
| $10^{-6}$ | | | | | | | | | −6 |
| $3 \times 10^{-6}$ | | | | | | | | | −33 |
| $10^{-5}$ | +11 | | | | −6 | | | 0 | −92 |
| $3 \times 10^{-5}$ | −4 | | | −13 | −41 | | | | |
| $10^{-4}$ | +25 | | | | | | | 0 | |
| (b) Vaso-dilator activity (Ringer-Norfenefrin solution) | | | | | | | | | |
| $10^{-7}$ | | | +3 | +7 | | | | | |
| $10^{-6}$ | | +1 | +29 | +4 | | | +12 | | |
| $3 \times 10^{-6}$ | | +39 | | | | | | | |
| $10^{-5}$ | | +93 | +58 | | | | +79 | +41 | |
| $3 \times 10^{-5}$ | | | | +12 | +47 | +19 | +67 | | 0 |
| $10^{-4}$ | | +147 | | | | | | +87 | (++) |

(++) A control test was carried out with heptaminol, which resulted in constriction

TABLE 6

Relative change in coronary blood flow in the isolated guinea-pig heart (Langendorff)

| Serial no. μg | 1 | 2 | 3 | 4 | 5 | 6 | 10 | 15 | 16 | Heptaminol (comp.) | Aescin sodium salt (comp.) |
|---|---|---|---|---|---|---|---|---|---|---|---|
| 10 | +53/−14 | +17 | +14 | +31 | +118 | +129 | +33 | | +55 | 0 | −8 |
| 30 | +130/−11 | +72 | +19 | +76 | +280 | +187 | +68/−21 | | +61 | 0 | −38 |

TABLE 6-continued

| Relative change in coronary blood flow in the isolated guinea-pig heart (Langendorff) | | | | | | |
|---|---|---|---|---|---|---|
| 100 | +120 | +30 | +125 | | +85/−17 | 0 |

| Serial no. μg | 17 | 19 | 21 | 22 | 26 | 28 | 29 | 30 | Hept-aminol (comp.) | Aescin sodium salt (comp.) |
|---|---|---|---|---|---|---|---|---|---|---|
| 10 | + 86 | +30/−15 | +22 | + 63 | +28 | + 29 | + 52 | +158 | 0 | − 8 |
| 30 | +138 | +71/−10 | +23 | +109 | +57 | +118 | +111 | +211 | 0 | −38 |
| 100 | | | | | | +226 | | +232 | 0 | |

TABLE 7

| | Histamine rash test | | | | | | | | | Aescin sodium salt (comparison) |
|---|---|---|---|---|---|---|---|---|---|---|
| mg/kg i.p. | Serial no. | | | | | | | | | |
| | 2 | 3 | 4 | 22 | 25 | 26 | 27 | 28 | 29 | 31 | |
| 0.1 | 3.5 | | | | | | | | | |
| 0.3 | 3.4 | | | | | | | | | |
| 1.0 | 2.6 | 2.5 | 3.1 | 2.6 | | 1.8 | 3.6 | | 3.3 | | 2.2 |
| 2.5 | | | | | | | | | | | 3.8 |
| 3.0 | 1.7 | 2.5 | 1.7 | 1.3 | 1.3 | 1.2 | 1.9 | 2.9 | 1.7 | | |
| 10.0 | 1.9 | | | | | 1.4 | | | | 2.6 | |

TABLE 8

| | Toxicity in the mouse (mg/kg) | | | | | | | | | | Aescin sodium salt (comparison) |
|---|---|---|---|---|---|---|---|---|---|---|---|
| Mode of administration | | | | | | | | | | | |
| Serial no. | 1 | 2 | 3 | 4 | 7 | 8 | 9 | 11 | 12 | 13 | 14 | |
| i.v. | | 11,7 | 10,8 | 12,4 | | | | | | | | 1,4–3,2 |
| i.p. | 50–100 | 114 | 50–100 | 50–100 | 100–250 | 25–100 | 100–250 | 100–250 | 100–250 | 100–250 | 50–100 | 5–10 |
| p.o. | | 940 | | | | | | | | | | 134–320 |

| Serial no. | 15 | 16 | 17 | 18 | 19 | 20 | 21 | 22 | 23 | 24 | 25 | |
|---|---|---|---|---|---|---|---|---|---|---|---|---|
| i.v. | | | | | | | | | | | | 1,4–3,2 |
| i.p. | 50–100 | 50–100 | 25–50 | 50–100 | 100–250 | 50–100 | 50–100 | 25–50 | 100–250 | 50–100 | 50–100 | 5–10 |
| p.o. | | | | | | | | | | | | 134–320 |

| Serial no. | 26 | 27 | 28 | 29 | 30 | 31 | | |
|---|---|---|---|---|---|---|---|---|
| i.v. | | | | | | | 50–100 | 1,4–3,2 |
| i.p. | 50–100 | 100–250 | 50–100 | 50–100 | 100–250 | | | 5–10 |
| p.o. | | 2400 | | | | | | 134–320 |

TABLE 9

Suppression of carrageenin oedema in the paw (%)
3 h p.a.(antiphlogistic activity)

| mg/kg p.o. | Serial no. | | | | | |
|---|---|---|---|---|---|---|
| | 2 | 3 | 4 | 7 | 13 | 26 | 31 |
| 25 | 53 | | | 53 | | | |
| 63 | 52 | | | 71 | 17 | | |
| 100 | 46 | 11 | 14 | | | 59 | 39 |
| 200 | | | | | | | 26 |

TABLE 10

Suppression of writhing movements %

| mg/kg p.o. | Serial no. | | | | |
|---|---|---|---|---|---|
| | 2 | 7 | 8 | 25 | 26 |
| 40 | 32 | 46 | | | |
| 50 | 53 | | 15 | 46 | 45 |
| 63 | 51 | 67 | | | |
| 100 | 80 | 77 | | | |

Discussion of the Results

According to Tables 2 and 3, the compounds according to the invention, particularly compound 26 in Table 2 and compound 27 in Table 3, show a stronger vasotonic activity than the comparison substance aescin sodium.

The results according to Table 4 agree with the findings in the preceding Tables. In the isolated portal vein, the substances according to the invention—particularly compounds 2 and 22—induce a distinctly stronger increase in vasotonus than the comparison substance heptaminol.

The effects on the perfused rabbit ear, (see Table 5) are especially favourable in comparison with aescin sodium. Thus the compounds according to the invention, according to Table 5a, do not show any vasospasms. Aescin sodium, however, even at a concentration of $10^{-5}$ g/ml, causes vasospasms almost leading to vein closure (see Table 5a).

In organs with tonicising vessels, the compounds according to the invention, dilate the vessels to an extent which depends on the concentration of the compounds, both in the rabbit ear perfused with Ringer-Norfenefrin solution (see Table 5b) and in the perfused guinea-pig heart (see Table 6). In comparison the substance heptaminol intensifies the Ringer-Norfenefrin constriction in the rabbit ear (see Table 5b) and has no effect on the guinea-pig heart (see Table 6). The comparison substance aescin sodium has no effect on the tonicised rabbit ear (see Table 5b) and has a constrictor effect on the coronary vessels in the guinea-pig heart.

As the histamine-rash test according to Table 7 shows, the compounds according to the invention induce a significant improvement in the suppression of increased capillary permeability caused by histamine than does aescin sodium.

Toxicity in the mouse of the compounds according to the invention (see Table 8) is significantly more favourable than that of aescin sodium. Tests with rabbits also show analogous results.

Certain of the compounds according to the invention have an inflammation-suppressing and anti-oedematous activity as shown in the tests on carrageenin and serotonin oedemas in the rat paw (see Table 9). Certain of the compounds also have an analgestic activity as shown in the Writhing test (see Table 10) and the Hot-plate test.

Thus the activity spectrum of the compounds according to the invention which we have tested make them particularly valuable as vaso-active agents.

According to a still further feature of the present invention there are provided pharmaceutical compositions comprising as active ingredient at least one compound of formula I as hereinbefore defined or physiologically compatible acid addition salt thereof in association with a pharmaceutical carrier or excipient.

The compositions may be presented in a form suitable for oral, rectal, parenteral or topical administration for veterinary use. Thus suitable forms of administration include for example powders, tablets, coated tablets, capsules, solutions including injection solutions, pastes, suspensions and suppositories, such compositions containing solid or liquid carriers or excipients conventionally used in the pharmaceutical art such as starch, lactose, cellulose derivatives, stearic acid and salts thereof, solvents, solubilising agents, suppository masses and chlorides, phosphates and carbonates, for example sodium carbonate.

The compositions are advantageously presented in the form of dosage units, each dosage unit being adapted to supply a fixed dose of active ingredient. Thus compositions for oral administration are conveniently presented as dosage units containing 25 to 50 mg of active ingredient for administration 2-3 times daily. Compositions for parenteral administration may be presented for administration either in a single injection or as a prolonged infusion in dosage of 10 to 20 mg per day.

The following Examples serve to illustrate the preparation of the new compounds according to the invention. The Serial Nos. refer to the enclosed Table I.

EXAMPLE 1

2-(2,3,5,6-Tetramethylbenzyl)-aminoheptane hydrochloride (Serial Number 1)

36.5 g (0.2 mol) of 2,3,5,6-tetramethylbenzyl chloride, 46.0 g (0.4 mol) of 2-aminoheptane and 100 ml of benzene are refluxed for 2 hours. The solvent is then removed in vacuo. A solution of 8 g (0.2 mol) of sodium hydroxide in methanol is then added to the residue to liberate the free base. The reaction product is separated from the precipitated sodium chloride by means of a suction filter, and the excess of 2-aminoheptane is removed by vacuum distillation. The 2-(2,3,5,6-tetramethylbenzyl)aminoheptane obtained is then treated with ethereal hydrochloric acid to convert it into the hydrochloride which is recrystallised from methanol/ethyl acetate. The melting point of the hydrochloride is 155° C.

Yield: 55.4 g (93% of theory).

EXAMPLE 2

2-(2,4,6-Trimethylbenzyl)-aminoheptane hydrochloride (Serial Number 2)

A solution of 168.7 g (1 mol) of 2,4,6-trimethylbenzyl chloride in 250 ml of toluene is mixed with a solution of 230.4 g (2 mol) of 2-aminoheptane in 250 ml of toluene, and the reaction mixture is refluxed for 2 hours. After evaporation of the toluene in vacuo, the evaporation residue is thoroughly mixed with a solution of 50 g of sodium hydroxide in 500 ml of water. The organic phase is extracted with methylene chloride. The methylene chloride solution is dried over anhydrous sodium sulphate and evaporated in vacuo. The evaporation residue is fractionated under vacuum and yields, in addition to 115 g of 2-aminoheptane 236 g (95.5% of theory) of 2-(2,4,6-trimethylbenzyl)-aminoheptane of boiling point 175°–178° C. (at 12 Torr). The base is treated with ethereal hydrochloric acid and the title compound 2-(2,4,6-trimethylbenzyl)-aminoheptane hydrochloride is obtained. This compound is recrystallised from methylene chloride/ether (1:1) to yield crystals having a melting point of 167° C. The experiment is repeated three times replacing 1 mol of 2-aminoheptane by 1 mol of the inert tertiary bases, triethylamine, tributylamine and diisopropylamine.

The course of each reaction may be followed by thin-layer chromatography:

| | |
|---|---|
| Stationary phase: | silica gel $F_{254}$ plates (5 × 20 cm) [manufactured by E. Merck, Darmstadt], |
| Eluent: | I chloroform/methanol/85% formic acid (85:10:5 parts by volume) II chloroform/methanol (90:10) |
| Length of flow: | 10 cm |
| Detection: | extinction of fluorescence |
| $R_f$(at chamber saturation) | I 0.54 II 0.68 |

EXAMPLE 3

2-[Dimethylphosphinylmethyl (2,4,6-trimethylbenzyl)]aminoheptane hydrochloride (Serial Number 30)

(a) 12.4 g (0.05 mol) of 2-(2,4,6-trimethylbenzyl)-aminoheptane (Example 2) and 6.4 g (0.05 mol) of chloromethyl dimethyl phosphine oxide in a solvent mixture of 100 ml of toluene and 50 ml of dimethylformamide are heated in the presence of 7.5 g of triethylamine at a bath temperature of 135° C. The end point of the reaction is detected chromatographically. After removal of the triethylamine, solvent and the triethylamine hydrochloride formed, the reaction product is taken up in ethyl acetate. A slight excess of an ethereal hydrochloric acid solution is added and 2-[dimethylphosphinylmethyl (2,4,6-trimethylbenzyl)]-aminoheptane hydrochloride is obtained as crystals.

Melting point: 123° C., yield: 17.2 g (92% of theory).

(b) The reaction is carried out analogously to Example (3a) but using 10.3 g (0.05 mol) of N-(dimethylphosphinylmethyl)-2-aminoheptane and 8.5 g (0.05 mol) of 2,4,6-trimethylbenzyl chloride, (c) The reaction is carried out analogously to Example (3a) but using 12.0 g (0.05 mol) of N-dimethylphosphinylmethyl (2,4,6-trimethylbenzyl)-amino and 9.0 g (0.05 ml) of 2-bromoheptane.

The hydrochlorides obtained according to Examples 3(a),(b) and (c) are identical.

EXAMPLE 4

2-(2,4,6-Trimethylbenzyl)-aminoheptane hydrochloride (Serial Number 2)

2.8 g (0.01 mol) of (2,4,6-trimethylbenzyl)-2-heptylthioamide are desulphurised in 100 ml of 80% aqueous ethanol with 3 g of Raney nickel at boiling temperature over a period of 3 hours. The Raney nickel and solvent is removed to yield 2-(2,4,6-trimethylbenzyl)-aminoheptane having a boiling point of 175°–178° C. (at 12 Torr.). The hydrochloride is prepared therefrom analogously to Example 2. The product is identical to the product prepared in Example 2 in all its physical properties. Yield: 2.2 g (90% of theory).

EXAMPLE 5

2-(2,4,6-Trimethylbenzyl)-aminoheptane hydrochloride (Serial Number 2)

14.8 g of 2,4,6-trimethylbenzaldehyde and 11.5 g of 2-aminoheptane are refluxed in about 100 ml of benzene, using a water-separator, until 1.8 ml of water have been removed. The benzene is removed in vacuo and the oil remaining is dissolved in approximately 200 ml of methanol. 19.0 g of sodium hydride are added in small portions, the mixture being shaken continuously. After standing over night, about 200 ml of water are added and the oil which precipitates out is extracted with methylene chloride. The organic extract is dried over sodium sulphate, evaporated, and the oil remaining is dissolved in ether. Ethereal hydrochloric acid is then added and the desired product precipitates out and is then recrystallised from methylene chloride/ether. Melting point: 167° C., Yield: over 80%.

EXAMPLE 6

2-[Ethyl (2,4,6-trimethylenzyl)]-aminoheptane hydrochloride (Serial Number 32)

In a tightly sealed three-necked flask which is flooded with dry nitrogen from one side and connected to a wash bottle containing acetone on the other side, 1.7 g (0.045 mol) of sodium borohydride are suspended in 37 ml of diethylene glycol dimethyl ether by stirring using a magnetic stirrer. Then 14.5 g (0.05 mol) of 2-[N-acetyl (2,4,6-trimethylbenzyl)]aminoheptane are added. While the nitrogen atmosphere is retained, 7.8 g (0.055 mol) of boron trifluoride etherate are added dropwise to the stirred suspension at room temperature over a period of one hour. The mixture is stirred for a further hour. Subsequently, 30 ml of concentrated hydrochloric acid and 100 ml of water are added, still under a nitrogen atmosphere. Any diborane present in the flask is forced into the wash bottle containing acetone by means of the nitrogen and is destroyed. The reaction mixture is evaporated in vacuo and the residue is treated with ethanol.

Inorganic salts are removed by suction filtration. The filtrate is mixed with an excess of 20% sodium hydroxide solution and the organic phase is extracted with ether. The solution is dried over sodium sulphate, evaporated down to a small volume and then mixed with an excess of ethereal hydrochloric acid. After a short time the desired end product crystallises out. It is suction filtered and the colourless out. It is suction filtered and the colourless crystals are dried quickly in a high vacuum over diphosphorus pentoxide. By further evaporation of the ethereal solution, a second yield of 2-[ethyl (2,4,6-trimethylbenzyl)]-aminoheptane hydrochloride, melting point 119° C., is obtained.

The product is examined by thin-layer chromatography using eluent I (see Example 2) and has an $R_f$ value of 0.45.

The experiment is repeated using 2-[N-propionyl (2,4,6-trimethylbenzyl)] aminoheptane in the place of the N-acetyl compound and finally converting the product to the sulphuric acid addition salt. The product is 2-[n-propyl (2,4,6-trimethylbenzyl)] aminoheptane sulphuric acid salt (Serial Number 33) of melting point 105° C.

In addition to the specific compounds prepared in Examples 1–6 there were prepared various other compounds according to the invention as shown below.

Formula Sheet $$R^1-CH_2-N-R^2 \quad R^1-CH_2-X \quad HN-R^2$$
$$\qquad |\qquad\qquad\qquad\qquad\qquad\qquad |$$
$$\qquad R^3\qquad\qquad\qquad\qquad\qquad\qquad R^3$$
$$(I)\qquad\qquad (II)\qquad\qquad (III)$$

$$X-R^2 \quad R^1-CH_2-NH \quad$$
$$\qquad\qquad\qquad\qquad |$$
$$\qquad\qquad\qquad\qquad R^3$$
$$(IV)\qquad (V)\qquad (VI)$$

$$R^1-CH_2-N-R^2 \quad R^1-CH=N-R^2 \quad R^1-CH_2-N=R^8$$
$$\qquad\qquad |$$
$$\qquad\qquad H$$
$$(VII)\qquad (VIII)\qquad (IX)$$

$$R^1-C-N-R^2 \quad R^1-CH_2-N-C-R^6 \quad R^1-CH_2-N-R^2$$
$$\quad \| \quad |\qquad\qquad\qquad |\quad \|\qquad\qquad\qquad |$$
$$\quad O\quad R^3\qquad\qquad\qquad R^3\ O\qquad\qquad\qquad C=O$$
$$\qquad\qquad\qquad\qquad\qquad\qquad\qquad\qquad\qquad\qquad |$$
$$\qquad\qquad\qquad\qquad\qquad\qquad\qquad\qquad\qquad\qquad R^7$$
$$(X)\qquad\qquad (XI)\qquad\qquad (XII)$$

$$R^1-C-N-R^2 \qquad\qquad R^4$$
$$\quad \|\quad |\qquad\qquad\qquad\ \diagup$$
$$\quad S\quad R^3\qquad\qquad -P$$
$$\qquad\qquad\qquad\qquad\qquad \|\ \diagdown R^5$$
$$\qquad\qquad\qquad\qquad\qquad O$$
$$(XIII)\qquad (XIV)$$

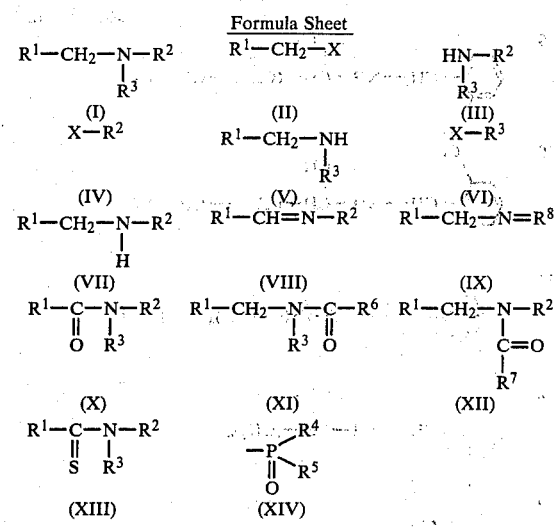

| Serial No. | Formula | m.p. | Prepared according to Example |
|---|---|---|---|
| 1 | H₃C, CH₃ ring—CH₂—NH—CH(CH₃)—(CH₂)₄—CH₃ . HCl (H₃C, CH₃) | 155° | 1 |
| 2 | CH₃ ring (H₃C—, —CH₃, CH₃)—CH₂—NH—CH(CH₃)—(CH₂)₄—CH₃ . HCl  racemate | 167° | 2,4,5 |
| 3 | CH₃ ring (H₃C—, —CH₃, CH₃)—CH₂—NH—CH(CH₃)—(CH₂)₄—CH₃  dextrorotatory . HCl | 163° | 1 |

-continued

| Serial No. | Formula | m.p. | Prepared according to Example |
|---|---|---|---|
| 4 | 2,4,6-tri-CH$_3$-C$_6$H$_2$-CH$_2$-NH-CH(CH$_3$)-(CH$_2$)$_4$-CH$_3$ · HCl (levorotatory) | 161° | 1 |
| 5 | 4-tert-butyl-2,6-di-CH$_3$-C$_6$H$_2$-CH$_2$-NH-CH(CH$_3$)-(CH$_2$)$_4$-CH$_3$ · HCl | 165° | 2 |
| 6 | 2-CH$_3$-5-tert-butyl-C$_6$H$_3$-CH$_2$-NH-CH(CH$_3$)-(CH$_2$)$_4$-CH$_3$ · HCl | 130° | 2 |
| 7 | 4-F-C$_6$H$_4$-CH$_2$-NH-CH(CH$_3$)-(CH$_2$)$_4$-CH$_3$ · HCl | 144° | 1 |
| 8 | 4-Cl-C$_6$H$_4$-CH$_2$-NH-CH(CH$_3$)-(CH$_2$)$_4$-CH$_3$ · HCl (dextrorotatory) | 193° | 1 |
| 9 | 2-Cl-C$_6$H$_4$-CH$_2$-NH-CH(CH$_3$)-(CH$_2$)$_4$-CH$_3$ · HCl | 89° | 1 |
| 10 | 2,6-di-Cl-C$_6$H$_3$-CH$_2$-NH-CH(CH$_3$)-(CH$_2$)$_4$-CH$_3$ · HCl | 121° | 1 |
| 11 | 3-Br-C$_6$H$_4$-CH$_2$-NH-CH(CH$_3$)-(CH$_2$)$_4$-CH$_3$ · HCl | 150° | 1 |
| 12 | 2-Br-C$_6$H$_4$-CH$_2$-NH-CH(CH$_3$)-(CH$_2$)$_4$-CH$_3$ · HCl | 75° | 2 |
| 13 | 4-O$_2$N-C$_6$H$_4$-CH$_2$-NH-CH(CH$_3$)-(CH$_2$)$_4$-CH$_3$ · HCl | 89° | 2 |
| 14 | 2,4,6-tri-CH$_3$-C$_6$H$_2$-CH$_2$-NH-(CH$_2$)$_4$-CH$_3$ · HCl | 140° | 1 |
| 15 | 2,4,6-tri-CH$_3$-C$_6$H$_2$-CH$_2$-NH-(CH$_2$)$_5$-CH$_3$ · HCl | 135° | 1 |
| 16 | 2,4,6-tri-CH$_3$-C$_6$H$_2$-CH$_2$-NH-(CH$_2$)$_6$-CH$_3$ · HCl | 135° | 1 |
| 17 | 2,4,6-tri-CH$_3$-C$_6$H$_2$-CH$_2$-NH-(CH$_2$)$_7$-CH$_3$ · HCl | 123° | 1 |

-continued
| Serial No. | Formula | m.p. | Prepared according to Example |
|---|---|---|---|
| 18 | 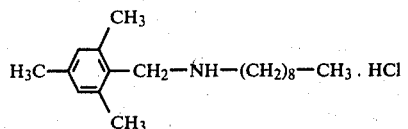 | 120° | 2 |
| 19 | 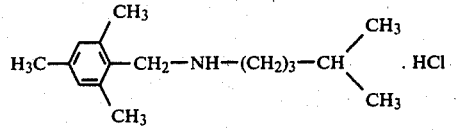 | 174° | 2 |
| 20 | 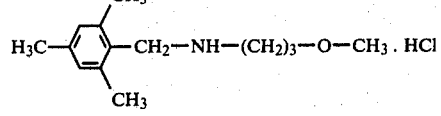 | 155° | 2 |
| 21 | 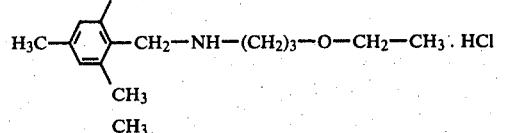 | 100° | 2 |
| 22 | 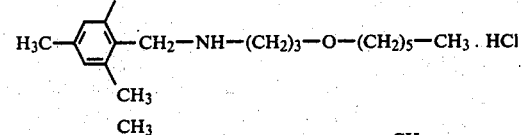 | 134° | 2 |
| 23 | 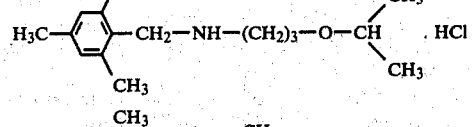 | 140° | 1 |
| 24 | 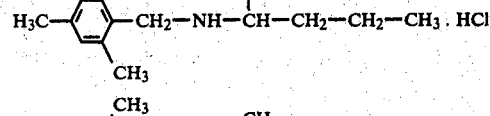 | 178° | 2 |
| 25 | 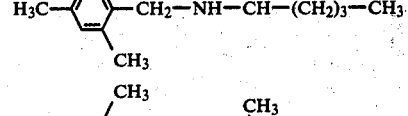 | Kp. 102° bei 0,1 Torr | 2 |
| 26 | 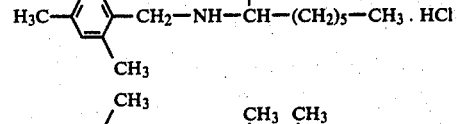 | 142° | 2 |
| 27 | 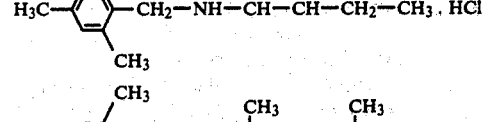 | 185° | 2 |
| 28 | 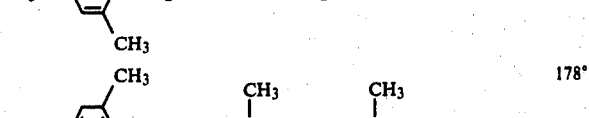 | 178° | 2 |
| 29 | 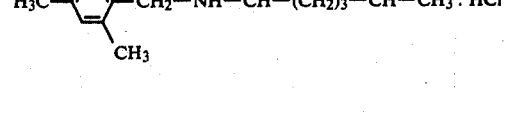 | 178° | 2 |

| Serial No. | Formula | m.p. | Prepared according to Example |
|---|---|---|---|
| 30 | ![structure] H₃C-(2,4,6-trimethylphenyl)-CH₂-N(CH₃)(CH₂-P(=O)(CH₃)₂)-CH-(CH₂)₄-CH₃ · HCl | 123° | 3 |
| 31 | H₃C-(2,4,6-trimethylphenyl)-CH₂-NH-CH(CH₃)-(CH₂)₃-C(CH₃)₂-OH · 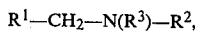cyclohexyl-NH-SO₃-H | 154° | 1 |
| 32 | H₃C-(2,4,6-trimethylphenyl)-CH₂-N(CH(CH₃)-(CH₂)₄-CH₃)(CH₂-CH₃) · HCl | 119° | 6 |
| 33 | H₃C-(2,4,6-trimethylphenyl)-CH₂-N(CH(CH₃)-(CH₂)₄-CH₃)(CH₂-CH₂-CH₃) · H₂SO₄ | 105° | 6 |

It is not intended that the examples given herein should be construed to limit the invention thereto, but rather they are submitted to illustrate some of the specific embodiments of the invention. Resort may be had to various modifications and variations of the present invention without departing from the spirit of the discovery or the scope of the appended claims.

What we claim is:

1. A pharmaceutical composition having vasotonia-regulating activity and comprising as active ingredient, in association with a pharmaceutical carrier or excipient, an effective amount of aralkylamine of the formula:

$$R^1-CH_2-N(R^3)-R^2,$$

wherein
$R^1$ is substituted phenyl, substitution of which is by: three or four alkyls, each having from 1 to 4 carbon atoms; the alkyls having a total of at most 6 carbon atoms, and any p-alkyl being separated from any other alkyl by a vacant m-position; 3,6-dialkyl, one alkyl having 4 carbon atoms, and the alkyls having a total of at most 6 carbon atoms; one bromine atom; or one nitro radical;

$R^2$
(a) has from 4 to 10 carbon atoms,
(b) is branched in the β-position (with reference to the nitrogen atom) only when there is also chain branching in the α-position,
(c) has no more than three chain branchings,
(d) has a single methyl substituent or no substituent in the α-position (with reference to the nitrogen atom) and is a member selected from the group consisting of $C_{5-10}$ alkyl having from 5 to 10 carbon atoms in one chain and is, optionally, monohydroxy substituted; alkyl having from 4 to 10 carbon atoms and interrupted by an oxygen atom when substitution of substituted phenyl, $R^1$, is by three or four alkyls, and
monohydroxy-substituted alkoxyalkyl having from 4 to 10 carbon atoms;
$R^3$ is —H, alkyl having from 1 to 4 carbon atoms or alkylene having from 1 to 4 carbon atoms and substituted by dialkylphosphinyl of the formula

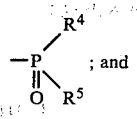 ; and each of $R^4$ and $R^5$ is alkyl; together they have a total of from 2 to 6 carbon atoms;
or an acid addition salt thereof.

2. A composition as claimed in claim 1 wherein each dosage unit contains 10 to 50 mg of active ingredient.

* * * * *